United States Patent [19]
Greene et al.

[11] Patent Number: 5,658,745
[45] Date of Patent: Aug. 19, 1997

[54] CELL ENUMERATION IMMUNOASSAY

[75] Inventors: Richard Alfred Greene, Westford, Mass.; Patricia Ann Kasila, Windham, N.H.; Mark Norman Bobrow, Lexington, Mass.

[73] Assignee: E. I. Du Pont de Nemours and Company, Wilmington, Del.

[21] Appl. No.: 390,598

[22] Filed: Feb. 17, 1995

[51] Int. Cl.$^6$ ................................................ C01N 33/566
[52] U.S. Cl. .................. 435/7.24; 435/7.92; 435/7.95; 435/967; 435/974; 424/534; 424/154.1; 436/524; 436/531; 436/541; 436/546; 436/548; 436/63; 436/172; 436/811
[58] Field of Search ........................ 435/7.24, 7.72, 435/7.8, 7.9, 7.92–7.95, 4, 967, 960, 963, 974; 424/529, 534, 154.1; 436/524, 528, 529, 531, 536, 541, 545, 546, 548, 501, 503, 63, 811, 823, 824, 172

[56] References Cited

U.S. PATENT DOCUMENTS

| 4,661,446 | 4/1987 | Schlossman et al. | 435/7.24 |
| 4,677,061 | 6/1987 | Rose et al. | 435/39 |
| 5,385,822 | 1/1995 | Melnicoff et al. | 435/5 |

FOREIGN PATENT DOCUMENTS

| 22948/88 | 4/1989 | Australia. | |
| 0311492 | 4/1989 | European Pat. Off. . | |
| 3811566A1 | 10/1988 | Germany . | |
| 90/04180 | 4/1990 | WIPO . | |
| 92/08981 | 5/1992 | WIPO . | |

OTHER PUBLICATIONS

Franke et al., Quantitative Determination of CD4/CD8 Molecules by a Cell Marker ELISA, *Clin. Chem.*, 40/1, pp. 38–42, 1994.

Carriere et al., An Immunoassay of CD4 and CD8 Antigens on the Surface of Lymphocytes of Healthy Volunteers and HIV Patients, *Int–Conf–AIDS*, 7(1), p. 259, Jun. 16–21, 1991.

Baumgarten, Horst, A cell ELISA for the quantitation of leukocyte antigens, *Journal of Immunological Methods*, 94, pp. 91–98, 1986.

Hessian et al., Development of an enzyme immunoassay for the quantitation of cellular antigen expression, *Journal of Immunological Methods*, 94, pp. 29–34, 1986.

*Primary Examiner*—Paula K. Hutzell
*Assistant Examiner*—Rachel Heather Freed

[57] ABSTRACT

This invention relates to a cell enumeration immunoassay which uses a calibrated standard, i.e., a substance which behaves like the sample under study and the concentration of which can be correlated to the concentration of the cells. This immunoassay is an efficient alternative to flow cytometry.

13 Claims, 3 Drawing Sheets

CELL ENUMERATION IMMUNOASSAY

FIELD OF THE INVENTION

This invention relates to an immunoassay and, more particularly, to a cell enumeration immunoassay as an efficient alternative to flow cytometry.

BACKGROUND OF THE INVENTION

With the development of Kohler and Milstein's hybridoma technology around 1975, monoclonal antibodies were utilized in the discovery and identification of cell surface molecules. Cell marker analyses are important in the prognosis, classification of state of disease, treatment decisions, and monitoring of therapy. For example, in human immunodeficiency virus (HIV) infection, both the $CD4^+$/$CD8^+$ T-cell ratio and the absolute number of $CD4^+$ T lymphocytes are important for the reasons noted above. The functions of cell membrane molecules and the consequences of their quantitative changes in several disorders (e.g., septicemia, burns, autoimmune diseases, graft rejection) are better understood because of advances in techniques in molecular biology and in the ability to assess the state of the immune system and to give more accurate prognoses.

Cell membrane markers are usually assayed by flow cytometry using a fluorescence-activated cell sorter (FACS) and a fluorescently labeled monoclonal antibody specific for the cell marker to be assayed. A FACS analysis measures cells as they flow through a flow cytometer in single file, or the best approximation thereof that can be achieved, in a fluid stream. Standardization and reproducibility of tests for clinical application is difficult, especially when measuring quantitative cellular fluorescence intensity, because different flow cytometers differ in sensitivity. In addition, the instrument is expensive (frequently >$200,000) and is labor intensive, requiring highly trained personnel to run the FACS. FACS analysis is also unreliable due to instrument variables and due to the way results are expressed. Usually, the results are expressed in units which require a separate determination of the number of white blood cells per μL of blood and a differential count. This combines the variability of three tests into one clinical result. Consequently, it would not be unusual for the same sample to give results differing by a factor of two in two separate determinations.

Given the foregoing, researchers have endeavored unsuccessfully to reliably determine markers in or on cells using enzyme immunoassays as an alternative to flow cytometry.

Franke et al., Clin. Chem., 40(1): 38–42 (1994) and AIDSLINE, December 1993 reporting on the Int-Conf-AIDS, page 259 (June 16–21, 1991) describe a cell marker ELISA, Capcellia™ CD4/CD8, to quantitatively determine CD4/CD8 molecules. The assay is performed in a single step on microtiter plates, specifically, cells are immobilized on the solid phase using pan-T monoclonal antibodies adsorbed on the solid phase surface along with simultaneous labeling of CD4 or CD8 by peroxidase-labeled immunoconjugates. The results are expressed in molar concentrations of CD4 or CD8 molecules calculated from standard curves. The factors used to convert concentrations of CD4 molecules into cells per liter were only relative and were used as guides. Thus, this assay falls woefully short in being an efficient alternative to flow cytometry.

Other approaches include the following:

Baumgarten, J. Immunological Methods, 94: 91–98 (1986) describes the requirements for calibration of a cell ELISA for the quantitation of leukocyte antigens using air-dried and methanol-fixed cells which were attached to microplate wells. The test was standardized by measuring both the specific antigen and the amount of cellular protein in each single sample and was calibrated either with intact cells or isolated plasma membranes prepared from the cells under study.

Hessian et al., J. Immunological Methods, 91: 29–34 (1986) describes a cell-associated enzyme immunoassay as an alternative to FACS analysis by employing immunofiltration methodology and soluble complexes of alkaline phosphatase and monoclonal anti-alkaline phosphatase.

U.S. Pat. No. 4,661,466, issued to Schlossman et al. on Apr. 28, 1987, describes the use of a monoclonal antibody to distinguish subsets of cells on the basis of different degrees of reactivity with the monoclonal antibody.

Similarly, U.S. Pat. No. 4,677,061, issued to Rose et al. on Jun. 30, 1987, describes T-cell lymphocyte subset monitoring of immunologic disease. T-cell subsets are monitored for a designated pattern of epitopic sites associated with specific surface membrane proteins where ratios of cells having different patterns are determined by multi-parameter flow cytometric analysis, the ratios being indicative of a probable change in the immunologic disease.

WO 90/04180, published Apr. 19, 1990, describes a method for measuring soluble CD4 antigens to diagnose a state of immune activation.

WO 92/08981, published May 29, 1992, describes the measurement of total leukocyte antigens and the use of such measurements to enumerate cells.

None of these references describes a standardized and reproducible cell enumeration immunoassay which is an efficient alternative to flow cytometry.

SUMMARY OF THE INVENTION

The present invention concerns a cell enumeration immunoassay for quantitating the number of cells in a subpopulation or a subset of the subpopulation of the total cell population in a sample which comprises:

(a) contacting a sample simultaneously with a modified solid phase, a first labeled antibody specific for the subpopulation and a second detectably labeled antibody specific for the subpopulation or the subset of the subpopulation wherein the label on the first antibody is used for immobilization onto the modified solid phase, the label on the second antibody is used for detection and the label on the first antibody is different from the label on the second antibody and further wherein the first antibody and the second antibody can have the same or different specificities and bind to different sites on the cells in the subpopulation;

(b) contacting separately a calibrated standard which can be labeled or unlabeled with the modified solid phase and (i) no other reactants if the calibrated standard is doubly labeled with the same labels attached to the first antibody and the second antibody of step (a), (ii) the first and second antibodies if the calibrated standard is unlabeled and capable of binding to the first and second antibodies, (iii) the first antibody only if the calibrated standard is singly labeled with the same label as the second antibody and is capable of binding with the first antibody, or (iv) the second antibody only if the calibrated standard is singly labeled with the same label as the first antibody and is capable of binding with the second antibody, provided that if the calibrated standard is a cell then it is labeled either singly or doubly with the same label or labels attached to the first and second antibodies;

(c) measuring separately a signal generated by step (a) and a signal generated by step (b); and (d) quantitating the number of cells in the subpopulation or subset of the subpopulation in the sample by comparing the results from the measurement of step (a) with the results obtained from the measurement of step (b).

In another embodiment the invention concerns a cell enumeration immunoassay for quantitating the number of T cells in a subset of the total T cell population in a sample which comprises:

(a) contacting the sample simultaneously with a modified solid phase, a labeled anti-pan T cell antibody wherein said label is used for immobilization onto the modified solid phase and a detectably labeled anti-subset specific antibody wherein the label on the anti-subset specific antibody is used for detection and is different from the label on the anti-pan T cell antibody and further wherein the anti-pan T cell antibody and the anti-subset specific antibody can have the same or different specificities and bind to different sites on the cells in the subpopulation;

(b) contacting separately a calibrated standard which can be labeled or unlabeled with the modified solid phase and; (i) no other reactants if the calibrated standard is doubly labeled with the same labels attached to the anti-pan T cell antibody and the anti-subset specific antibody of step (a), (ii) the anti-pan T cell antibody and the anti-subset specific antibody if the calibrated standard is unlabeled and capable of binding to both antibodies, (iii) the first antibody only if the calibrated standard is singly labeled with the same label as the anti-subset specific antibody and is capable of binding to the anti-pan T cell antibody, or (iv) the anti-subset specific antibody only if the calibrated standard is singly labeled with the same label as the anti-pan T cell antibody and is capable of binding with the anti-subset specific antibody, provided that if the calibrated standard is a cell then it is labeled either singly or doubly with the same label or labels attached to the antibodies;

(c) measuring separately a signal generated by step (a) and a signal generated by step (b); and (d) quantitating the number of T cells in the subset of the total T cell population in the sample by comparing the results from the measurement of step (a) with the results obtained from the measurement of step (b).

DETAILED DESCRIPTION OF THE INVENTION

Figure 1:
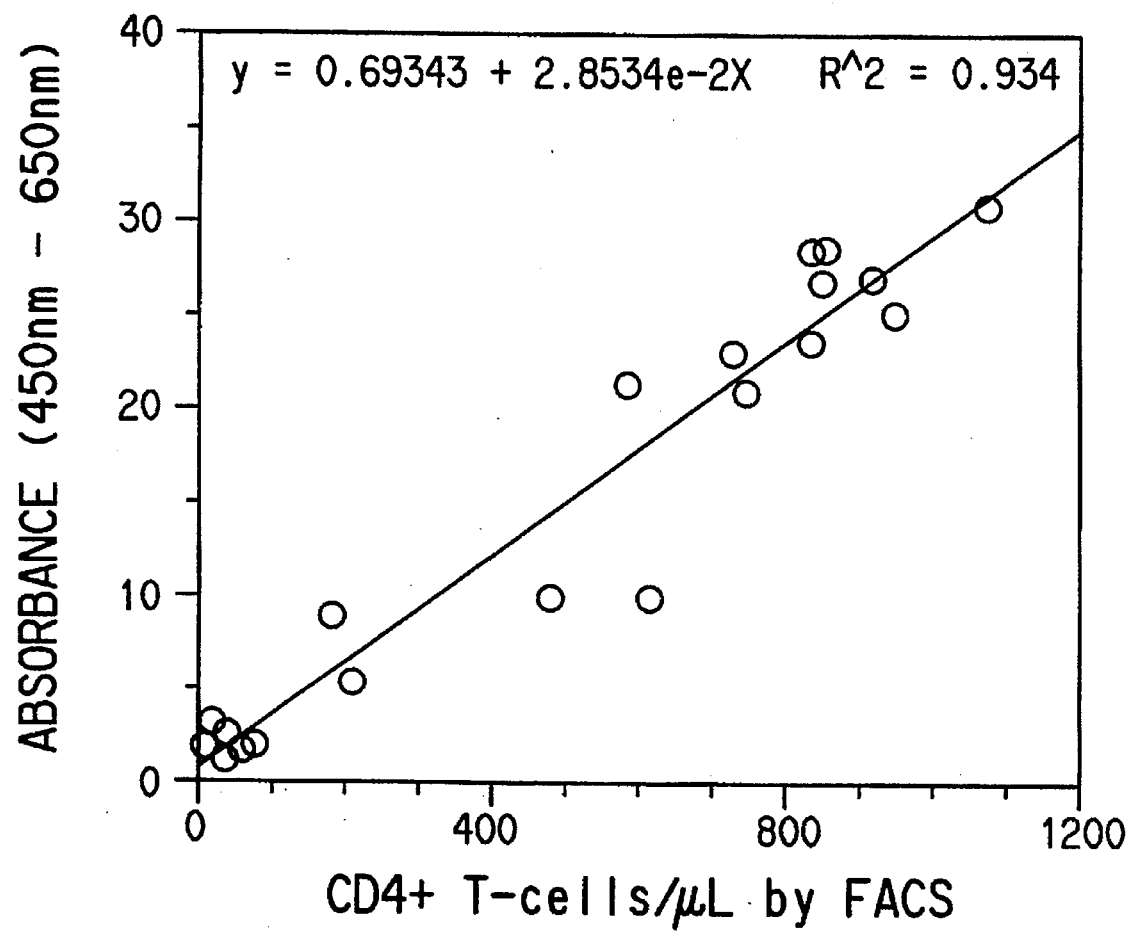
FIG. 1 is a standard curve of absorbance of the samples versus $CD3^+/CD4^+$ cells per μl of blood obtained by FACS analysis of the samples.
Figure 2:
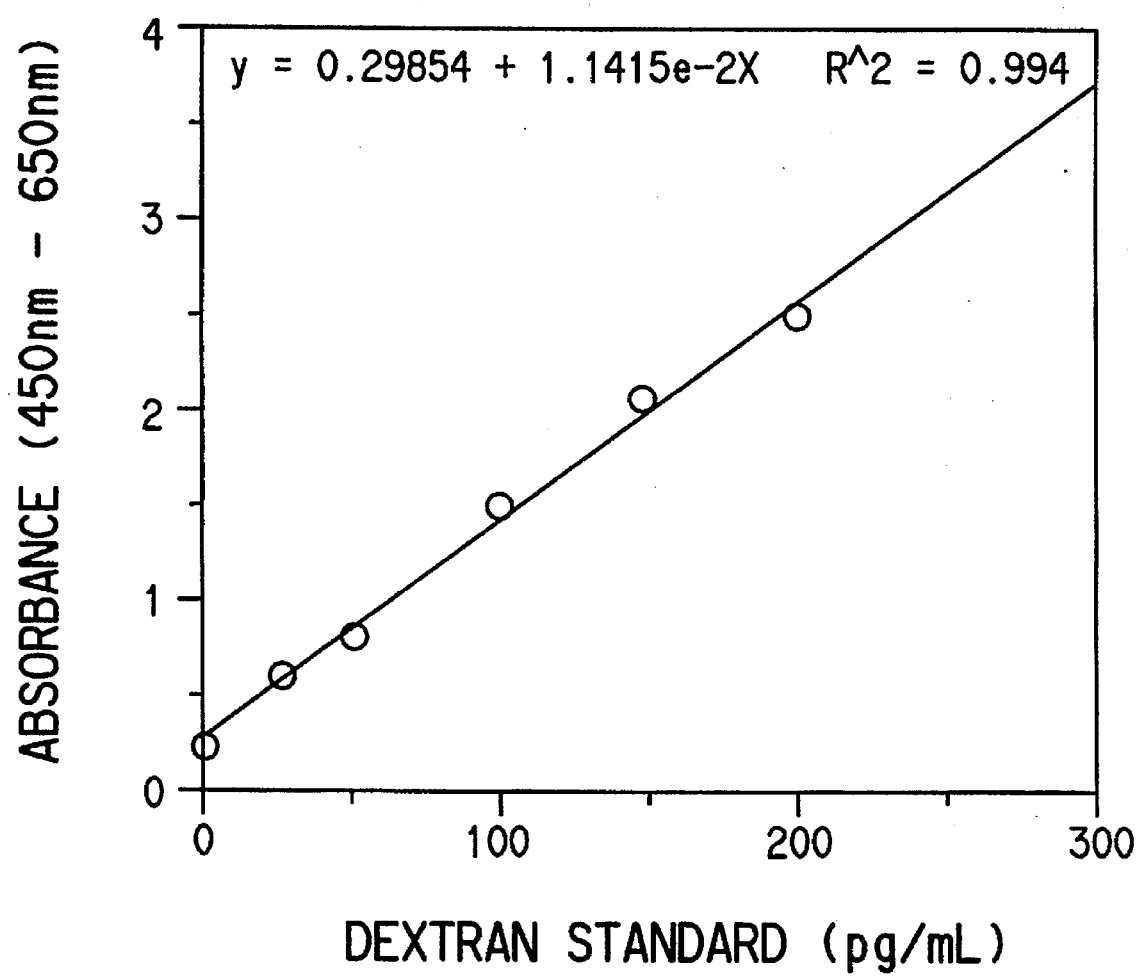
FIG. 2 presents the absorbance of the standard dilutions, i.e., the concentration of standard required to produce a given amount of absorbance.
Figure 3:
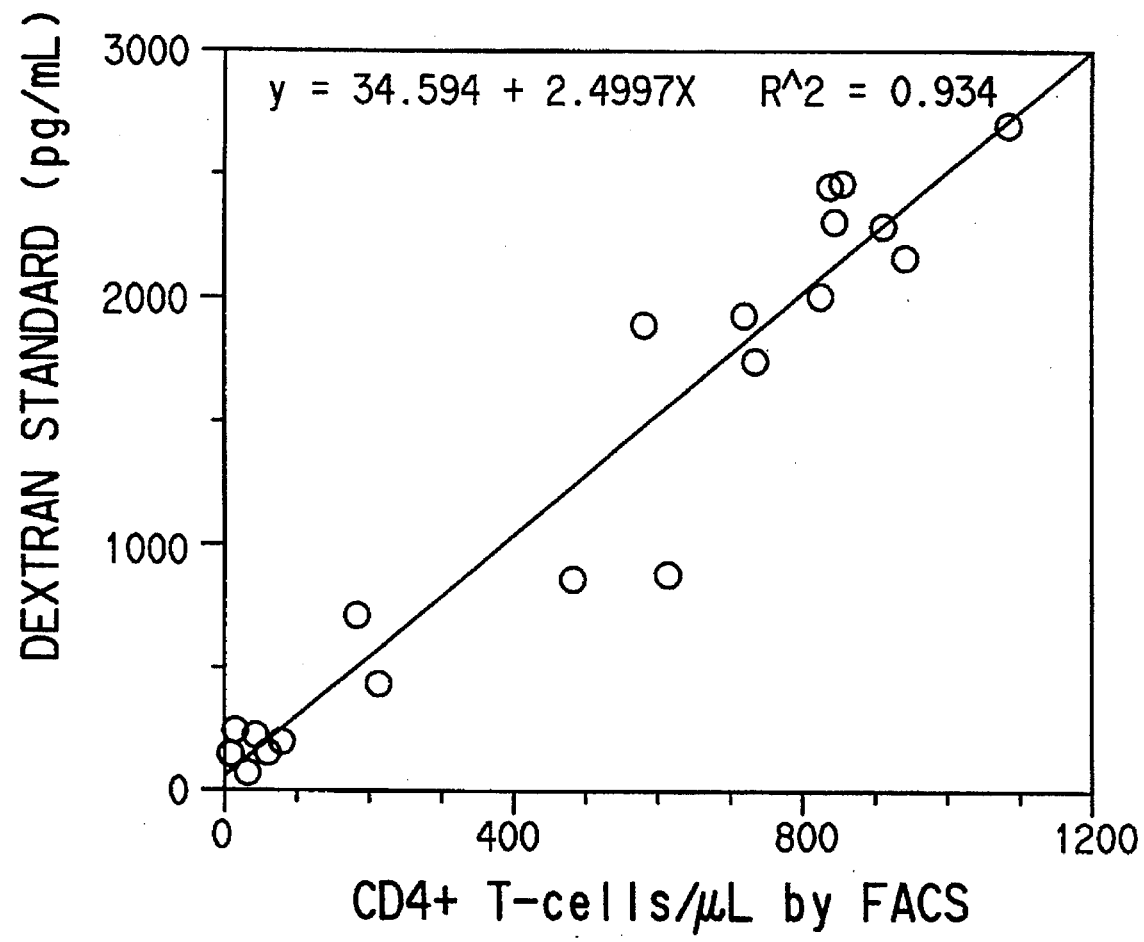
FIG. 3 shows the combination of the data presented in FIGS. 1 and 2 to calibrate the standard concentration in pg/mL versus the concentration of $CD3^+/CD4^+$ cells per μL of blood.

The term "calibrated standard" as used herein means a substance that behaves like the sample under study and the concentration of which can be correlated to the concentration of the cells. The substance can be a cell which is singly or doubly labeled, a particle or any other material which can be designed to function like the sample and the concentration of which can be correlated to the concentration of the cells in the sample.

The calibrated standard can be labeled or unlabeled provided that if the calibrated standard is a cell then it is labeled either singly or doubly. The calibrated standard reacts with the modified solid phase and no other reactants if the calibrated standard is doubly labeled with the same labels attached to the first and second antibodies. It reacts with the modified solid phase and the first and second antibodies if the calibrated standard is unlabeled and capable of binding to the first and second antibodies. It reacts with the modified solid phase and the first antibody only if the calibrated standard is singly labeled with the same label as the second antibody and is capable of binding with the first antibody. It reacts with the modified solid phase and the second antibody only if the calibrated standard is singly labeled with the same label as the first antibody and is capable of binding with the second antibody.

The standard can be calibrated using flow cytometry, a technique well known to those skilled in the art. Other methods of calibration include using immunocytochemistry or a cell counter.

Examples of substances which can be used as a calibrated standard include, but are not limited to, biotin and fluorescein labeled dextran, biotin and fluorescein labeled bovine serum albumin and biotinylated fluorescein. Biotin and fluorescein labeled dextran and biotinylated fluorescein are commercially available. Biotin and fluorescein labeled bovine serum albumin can be made using standard techniques as illustrated in the example below.

The cell enumeration immunoassay of the instant invention provides an accurate and efficient alternative to flow cytometry. It enables one to quantitate the number of cells in a subpopulation or a subset of the subpopulation of the total cell population in a sample such as blood or other cell containing specimen without the need for expensive instrumentation.

The cell enumeration immunoassay of the instant invention is a simultaneous solid phase or heterogeneous sandwich immunoassay in which the first labeled antibody, second detectably labeled antibody, modified solid phase and a sample are reacted together. The solid phase or support is modified so that it will bind with the first labeled antibody or capture reagent. Thus, the label on the first antibody is not used for detection but for immobilization onto the solid phase. Typically, the solid phase and first antibody are modified directly or indirectly with members of a specific binding pair which can be immune or non-immune. For example, if the solid phase is modified with streptavidin then the first antibody would be labeled with biotin. Modification of the solid phase is accomplished using techniques well known to those skilled in the art. Similarly, labeling of the first antibody involves techniques well known to those skilled in the art.

Immune specific binding pairs are exemplified by antigen/antibody systems or hapten/anti-hapten systems. There can be mentioned fluorescein/anti-fluorescein, biotin/anti-biotin, dinitrophenol/anti-dinitrophenol, etc. The antibody member, whether polyclonal, monoclonal or an immunoreactive fragment thereof, of the binding pair can be produced by customary methods familiar to those skilled in the art. The terms immunoreactive antibody fragment or immunoreactive fragment mean fragments which contain the binding region of the antibody. Such fragments may be Fab-type fragments which are defined as fragments devoid of the Fc portion, e.g., Fab, Fab' and $F(ab')_2$ obtained by reductive cleavage of the disulfide bonds connecting the heavy chain components of the intact antibody. If the antigen member of the specific binding pair is not immunogenic, e.g., a hapten, it can be covalently coupled to a carrier protein to render it immunogenic.

Non-immune binding pairs include systems wherein the two components share a natural affinity for each other but are not antibodies. Exemplary non-immune binding pairs are biotin-avidin or biotin-streptavidin, folic acid-folate binding protein, complementary probe nucleic acids, etc.

Suitable supports include synthetic polymer supports, such as polystyrene, polypropylene, substituted polystyrene, e.g., aminated or carboxylated polystyrene, polyacrylamides; polyamides; polyvinylchloride, etc.; glass beads; agarose; nitrocellulose; nylon; polyvinylidenedifluoride; surface-modified nylon, etc. The preferred support is a polystyrene microplate.

The second or detector antibody is detectably labeled with a label different from that on the first antibody. It can be labeled directly or indirectly with a member of an immune or non-immune specific binding pair as discussed above using conventional techniques. In order to facilitate signal detection, either the antibody or a member of a specific binding pair is labeled with a component of a reporting system. For example, the second antibody could be conjugated to fluorescein. Fluorescein can be detected directly or indirectly by using an enzyme-labeled anti-fluorescein antibody.

The term "reporting system" refers to the reporter selected and any means of linking the reporter to the antibody or to a component of a specific binding pair. Thus, a reporter can be linked directly or indirectly, covalently or non-covalently to an antibody or a member of a specific binding pair. Reporters may be radioactive isotopes, enzymes, fluorogenic, magnetic, chemiluminescent or electrochemical materials. Two commonly used radioisotopes are $^{125}$I and $^{3}$H. Standard radioactive isotopic labeling procedures include choramine T, lactoperoxidase and Bolton-Hunter methods for $^{125}$I and reductive methylation for $^{3}$H.

Enzymes are the preferred reporters. These include horseradish peroxidase, alkaline phosphatase, β-galactosidase, glucose oxidase, luciferase, β-lactamase, urease, and lysozyme. Labeling with enzymes is facilitated using dialdehyde, carbodiimide coupling, homobifunctional crosslinkers, etc. The labeling method chosen depends on the functional groups available on the enzyme and the material to be labeled, and the tolerance of both to the conjugation conditions. Labeling can be accomplished using any conventional methods including those described by Engvall and Pearlmann, Immunochemistry 8, 871 (1971), Avrameas and Ternynck, immunochemistry 8, 1175 (1971), Ishikawa et al., J. Immunoassay 4(3): 209–327 (1983) and Jablonski, Anal. Biochem. 148: 199 (1985). Labeling can be accomplished by indirect methods such as using spacers or other members of specific binding pairs. Detection of enzyme activity can be facilitated by measuring chromogenic, fluorogenic, magnetic, chemiluminescent or electrochemical changes by commonly known methods.

The first and second antibodies can have the same or different specificities and bind to different sites on the cells in the subpopulation.

The first and second antibodies can be polyclonal, monoclonal or an immunoreactive antibody fragment thereof as discussed above. Such antibodies and/or immunoreactive antibody fragments can be made using standard techniques well known to those skilled in the art.

After the sample has reacted with the modified solid phase, first labeled antibody and second detectably labeled antibody, it can be further subjected to treatment with an inactivation reagent, as described in the examples below, which serves to inactivate any endogenous peroxidases which may be present, fix the cells, and inactivate human immunodeficiency virus which might be present if the sample was obtained from a subject infected with HIV.

Any marker in or on a cell can be quantitatively determined using the instant cell enumeration immunoassay. Examples of cells which can be quantitatively determined using the cell enumeration immunoassay include CD4$^+$ T cells, CD8$^+$ T cells, B-cells, activated B cells, activated T cells, CMV-infected granulocytes, EBV infected B-cells, HIV infected monocytes, etc.

In a preferred embodiment, the instant invention concerns a T-Cell enumeration immunoassay for quantitating the number of T cells in a subset of the total T cell population in a sample which comprises:

(a) contacting the sample simultaneously with a modified solid phase, a labeled anti-pan T cell antibody wherein said label is used for immobilization onto the modified solid phase and a detectably labeled anti-subset specific antibody wherein the label on the anti-subset specific antibody is used for detection and is different from the label on the anti-pan T cell antibody and further wherein the anti-pan T cell antibody and the anti-subset specific antibody can have the same or different specificities and bind to different sites on the cells in the subpopulation;

(b) contacting separately a calibrated standard which can be labeled or unlabeled with the modified solid phase and; (i) no other reactants if the calibrated standard is doubly labeled with the same labels attached to the anti-pan T cell antibody and the anti-subset specific antibody of step (a), (ii) the anti-pan T cell antibody and the anti-subset specific antibody if the calibrated standard is unlabeled and capable of binding to both antibodies, (iii) the first antibody only if the calibrated standard is singly labeled with the same label as the anti-subset specific antibody and is capable of binding to the anti-pan T cell antibody, or (iv) the anti-subset specific antibody only if the calibrated standard is singly labeled with the same label as the anti-pan T cell antibody and is capable of binding with the anti-subset specific antibody, provided that if the calibrated standard is a cell then it is labeled either singly or doubly with the same label or labels attached to the antibodies.

(c) measuring separately the signal generated by step (a) and the signal generated by step (b); and (d) quantitating the number of T cells in the subset of the total T cell population in the sample by comparing the results from the measurement of step (a) with the results obtained from the measurement of step (b).

The anti-pan T cell antibody can be, by way of illustration, an anti-CD2 antibody or an anti-CD3 antibody. The preferred anti-pan T cell antibody is an anti-CD3 antibody. The CD3 antigen is called the T cell receptor (TcR). It has a complex multistranded structure and is involved in T cell activation in the immune response. It is found on virtually all mature T cells in the peripheral circulation as well as in precursor cells present in the thymus (thymocytes).

The anti-subset specific antibody can be an anti-CD4 antibody, anti-CD8 antibody, anti-CD25 antibody, etc. The preferred anti-subset specific antibody is an anti-CD4 antibody.

The CD4 antigen is found on about ⅔ of peripheral T-Cells (those which are CD8 negative) and also on monocytes and most thymocytes. Functionally, CD4 is an accessory molecule involved in the recognition of foreign antigens by T cells. The population of T cells which expresses CD4 is considered to represent the "helper" T cells. CD4 has been shown to be the cellular receptor necessary for binding of HIV to a cell during infection. As the disease progresses, the fraction of $CD4^+$ T lymphocytes in the blood decreases. The Center for Disease Control recommends that a level of less than 200 $CD4^+$ T cells per μL of blood be used in the case definition for AIDS. It is recommended that AIDS patients have their $CD4^+$ T cell levels measured 2–3 times per year. A level of less than 500 $CD4^+$ cells per μL of blood is frequently used as an indication for beginning antiviral therapy. The number of $CD4^+$ T cells is also commonly used as a criterion for admission of patients to clinical trials. The absolute number of $CD4^+$ T lymphocytes is important for prognosis, classification of state of disease, treatment decisions, and monitoring of therapy in human immunodeficiency virus (HIV) infection.

The following examples are intended to illustrate the invention and should not be construed as a limitation thereon.

EXAMPLE 1

Part A. Synthesis of Antibody Reagents

1. Anti-CD3-Biotin Antibody

An anti-CD3 monoclonal antibody solution (BioDesign) was dialyzed against 0.1M $NaHCO_3$ and then adjusted to 1 mg/ml in 0.1M $NaHCO_3$. Biotinamidocaproate, N-hydroxysuccinimide ester (Molecular Probes) was dissolved in dimethyl sulfoxide at 0.75 mg/ml. To 4 ml of antibody solution, 400 μl of biotin solution was added and mixed for 2 hours at room temperature, and then 400 μl of 2M tris-HCl, pH 8.0 was added and mixed for 15 minutes. The solution was dialyzed against phosphate buffered saline (PBS) at 4° C. and then 4 ml of 2% bovine serum albumin in PBS with 0.1% chloroacetamide was added.

2. Anti-CD4-Fluorescein Antibody

An anti-CD4 monoclonal antibody solution (Ancell) was adjusted to 1 mg/ml in 0.1M $NaHCO_3$ and then dialyzed against 0.1M $NaHCO_3$. 6-(fluorescein-5-(and-6) carboxamido) hexanoic acid, succinimidyl ester (Molecular Probes) was dissolved in dimethyl sulfoxide at 1 mg/ml. To 1 ml of antibody solution, 100 μl of fluorescein solution was added and mixed for 2 hours at room temperature, and then 100 μl of 2M tris-HCl, pH 8.0 was added and mixed for 30 minutes. The solution was dialyzed against phosphate buffered saline (PBS) at 4° C. and then 1 ml of 2% bovine serum albumin in PBS with 0.1% chloroacetamide was added.

Part B

Three tubes of EDTA blood were collected from 10 normal persons and 10 AIDS patients. One tube was analyzed for CD3+/CD4+ lymphocytes content by fluorescence-activated cell sorter (FACS) according to established procedures (Morbidity and Mortality Weekly Report, 1994 Revised Guidelines for the Performance of CD4+ T-Cell Determinations in Persons with Human Immunodeficiency Virus (HIV) infection, U.S. Department of Health and Human Services, Public Health Service, Centers for Disease Control, Vol. 43, No. R, Mar. 4, 1994). In brief, the cells are reacted with two fluorescently-labeled monoclonal antibodies that react with CD3 antigen and the CD4 antigen respectively if present on the cell surfaces. By definition, T cells have the CD3 antigen on their surface. The helper T cells (a subset of the total T cells that can be infected by HIV) have both CD4 and CD3. The FACS results are reported as the % of the total lymphocytes labeled with both fluorescent anti-CD3 monoclonal antibody and labeled with fluorescent anti-CD4 monoclonal antibody.

The second tube of EDTA blood was used for hematology analysis (total white cell count and differential count). The total white cell count was performed using an automated cell counter (Coulter) and is reported as total white cells/μL of blood. From microscopic examination of a stained slide, a manual differential count reports the % of the white cells that are morphologically lymphocytes. The combination of these two analyses yields the number of lymphocytes/μL of blood. Combining this result with the % of the lymphocytes that express CD3 and CD4 on their surfaces (the FACS result) allows the calculation of the number CD3+/CD4+ lymphocytes/μL of blood.

The third tube was tested using the cell enumeration immunoassay of the present invention as described below.

0.1 mL of blood was added to 1 mL of Lysing Reagent (1.68M ammonium chloride, 0.1M potassium bicarbonate, 1 mM EDTA, pH 7.4). After 5 minutes, the white blood cells were separated from the lysed red blood cells by a 10 second centrifugation at maximum speed in a microcentrifuge (Sorvall). A 1:5 dilution of the original white cells was prepared by resuspending the white cell pellet in 0.5 mL of Antibody Reagent (UCHT1 anti-CD3 monoclonal antibody [BioDesign] was labeled with biotin and QS4120 anti-CD4 monoclonal antibody [Ancell] was labeled with fluorescein. They were used at 5 μg/mL and 20 ng/mL, respectively in PBS containing 4% BSA and 0.09% chloroacetamide). A 1:25 dilution of the original white cells was also prepared by adding 0.1 mL of the 1:5 dilution of white cells to 0.4 mL of Antibody Reagent. For each of the dilutions (1:5 and 1:25) 0.1 mL samples were added to duplicate wells of a streptavidin-coated microplate (DuPont). Dilutions of a biotinylated and fluoresceinated dextran (the calibrated standard) (Molecular Probes) were also added to duplicate wells.

After 2 hours at room temperature, 0.05 mL of Inactivation Reagent (0.1% sodium azide, 0.002% sodium stannate, 0.01% hydrogen peroxide in 75% ethanol) were added to each well. During a 30 minute room temperature incubation, the Inactivation Reagent inactivated endogenous cellular peroxidases, inactivated any HIV particles from the sample, and fixed the cells. The microplate was then washed 6× with Plate Wash (DuPont) to remove unreacted antibodies.

To each well was added 0.1 mL of Detector Reagent (1:200 affinity-purified sheep antifluorescein polyclonal antibody labeled with HRP [Boehringer-Mannheim] in PBS containing 50% normal rabbit serum, 1% casein and 0.09% chloroacetamide). During a 30 minute room temperature incubation, the anti-fluorescein-HRP bound to any fluoresceinated anti-CD4 monoclonal antibody on the surface of cells that are bound to the streptavidin-coated microplate via the biotinylated anti-CD3 monoclonal antibody. The microplate was then washed 6× with Plate Wash Buffer to remove unreacted Detector Reagent.

To each well, 0.1 mL of TMB (tetramethylbenzidene) Substrate (Proteins International) was added. During a 1 hour room temperature incubation, any HRP in the wells generated a colorimetric signal from the TMB. To each well, 0.1 mL of TMB Stop (Proteins International) was added to stop the enzymatic reaction. The absorbance in each well was measured at 450 nm using a Molecular Devices plate reader with a 650 nm reference filter.

Part C. Calibration of the Standard

FACS results were combined with hematology results of the samples to generate a value for each sample in units of CD3+/CD4+ cells μL of blood.

The absorbance produced in the assay by a given sample may vary due to fluctuations in the assay. This can be controlled for by running the same concentrations of standard in each assay and generating a calibration curve (or standard curve).

Changes in the standard curve are used to correct the sample absorbance for assay variations by calculating the sample results in terms of the concentration of standard needed in that assay to produce the observed absorbance. So each sample result is equal to the result that would be obtained with a certain number of pg/mL of dextran standard.

Doing this experiment once and also testing a number of samples by FACS permits determination of the amount of pg/mL of dextran standard which corresponds to the number of CD3+/CD4+ cells/µL of blood. This does not change with assay variation.

Since the amount of pg/mL of dextran standard which corresponds to each sample is known, one can now calculate the number CD3+/CD4+ cells/µL of blood which corresponds to each sample.

EXAMPLE 2

Synthesis of Biotin and Fluorescein Labeled Bovine Serum Albumin 10 mg of bovine serum albumin (Sigma) were dissolved in 10 ml 0.1M $NaHCO_3$. 0.5 mg each of biotinamidocaproate, N-hydroxysuccinimide ester (Molecular Probes) and 6-(fluorescein-5-(and-6) carboxamido) hexanoic acid, succinimidyl ester (Molecular Probes) were dissolved in 1 ml dimethyl sulfoxide. The two solutions were mixed for 2 hours at room temperature and then dialyzed against phosphate buffered saline.

What is claimed is:

1. A cell enumeration immunoassay for quantitating the number of cells in a subpopulation or a subset of the subpopulation of a total cell population in a sample which comprises:

(a) contacting the sample simultaneously with a modified solid phase, a first labeled antibody specific for the subpopulation and a second detectably labeled antibody specific for the subpopulation or the subset of the subpopulation wherein the label on the first antibody is used for immobilization onto the modified solid phase, the label on the second antibody is used for detection and the label on the first antibody is different from the label on the second antibody and further wherein the first antibody and the second antibody can have the same or different specificities and bind to different sites on the cells in the subpopulation wherein when the first and the second antibodies have the same specificity then the cells in the subpopulation have more than one copy of an epitope to which the first and second antibody can bind;

(b) contacting separately a calibrated standard which can be labeled or unlabeled with the modified solid phase and (i) no other reactants if the calibrated standard is doubly labeled with the same labels attached to the first antibody and the second antibody of step (a), (ii) the first and second labeled antibodies if the calibrated standard is unlabeled and capable of binding to the first and second antibodies, (iii) the first labeled antibody only if the calibrated standard is singly labeled with the same label as the second antibody and is capable of binding with the first antibody, or (iv) the second labeled antibody only if the calibrated standard is singly labeled with the same label as the first antibody and is capable of binding with the second antibody, provided that if the calibrated standard is a cell then it is labeled either singly or doubly with the same label or labels attached to the first and second antibodies wherein when the cell is singly labeled said cell already has the other of the first or the second labels;

(c) measuring separately a signal generated by step (a) and a signal generated by step (b); and (d) quantitating the number of cells in the subpopulation or subset of the subpopulation in the sample by comparing the results from the measurement of signal generated by step (a) with the results obtained from the measurement of signal generated by step (b).

2. An immunoassay according to claim 1 wherein the cells to be quantitated are selected from the group consisting of $CD4^+$ T cells, $CD8^+$ T cells, B-cells, activated B cells, activated T cells, and CMV-infected granulocytes, EBV infected B-cells, and HIV infected monocytes.

3. A T cell enumeration immunoassay for quantitating the number of T cells in a subset of a total T cell population in a sample which comprises:

(a) contacting the sample simultaneously with a modified solid phase, a labeled anti-pan T cell antibody wherein said label is used for immobilization onto the modified solid phase and a detectably labeled anti-subset specific antibody wherein the label on the anti-subset specific antibody is used for detection and is different from the label on the anti-pan T cell antibody and further wherein the anti-pan T cell antibody and the anti-subset specific antibody have different specificities and bind to different sites on the cells in the subpopulation;

(b) contacting separately a calibrated standard which can be labeled or unlabeled with the modified solid phase and (i) no other reactants if the calibrated standard is doubly labeled with the same labels attached to the anti-pan T cell antibody and the anti-subset specific antibody of step (a), (ii) the labeled anti-pan T cell antibody and the labeled anti-subset specific antibody if the calibrated standard is unlabeled and capable of binding to both antibodies, (iii) the labeled anti-pan T cell only if the calibrated standard is singly labeled with the same label as the anti-subset specific antibody and is capable of binding to the anti-pan T cell antibody, or (iv) the labeled anti-subset specific antibody only if the calibrated standard is singly labeled with the same label as the anti-pan T cell antibody and is capable of binding with the anti-subset specific antibody, provided that if the calibrated standard is a cell then it is labeled either singly or doubly with the same label or labels attached to the antibodies wherein when the cell is singly labeled said cell already has the other of the labeled anti-pan T cell or the labeled anti-subset specific antibody;

(c) measuring separately a signal generated by step (a) and a signal generated by step (b); and (d) quantitating the number of T cells in the subset of the total T cell population in the sample by comparing the results from the measurement of signal generated by step (a) with the results obtained from the measurement of signal generated by step (b).

4. An immunoassay according to claim 3 wherein the cells to be quantitated in the subpopulation are $CD4^+$ T lymphocytes, the labeled anti-pan T cell antibody is a biotinylated anti-CD3 monoclonal antibody, the detectably labeled anti-subset specific antibody is a fluorescein labeled anti-CD4 monoclonal antibody and the calibrated standard is a biotin and fluorescein labeled dextran.

5. An immunoassay according to claim 1 or 3 wherein the solid phase is modified with a first member of a non-immune binding pair.

6. An immunoassay according to claim 1 or 3 wherein the solid phase is modified with a first member of an immune binding pair.

7. An immunoassay according to claim 5 wherein the first antibody is labeled with the second member of a non-immune binding pair.

8. An immunoassay according to claim 6 wherein the first antibody is labeled with the second member of an immune binding pair.

9. An immunoassay according to claim 1 or 3 wherein the second antibody is detectably labeled with a member of a non-immune binding pair.

10. An immunoassay according to claim 1 or 3 wherein the second antibody is detectably labeled with a member of an immune binding pair.

11. An immunoassay according to claim 1 or 3 wherein at least one of the antibodies is monoclonal.

12. An immunoassay according to claim 1 or 3 wherein the calibrated standard is selected from the group consisting of dextran labeled with biotin and fluorescein, bovine serum albumin labeled with biotin and fluorescein and biotinylated fluorescein.

13. An immunoassay according to claim 1 or 3 wherein the product of step (a) is reacted with an inactivation reagent to inactivate endogenous peroxidases, fix the cells in the sample and inactivate any human immunodeficiency virus which might be present in the sample.

* * * * *